(12) United States Patent
Salamone et al.

(10) Patent No.: US 7,423,131 B2
(45) Date of Patent: Sep. 9, 2008

(54) BUSULFAN IMMUNOASSAY

(75) Inventors: Salvatore J. Salamone, Stockton, NJ (US); Jodi Blake Courtney, Doylestown, PA (US); Shu He, Allentown, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 54 days.

(21) Appl. No.: 11/544,977

(22) Filed: Oct. 6, 2006

(65) Prior Publication Data

US 2007/0077608 A1   Apr. 5, 2007

Related U.S. Application Data

(62) Division of application No. 11/225,613, filed on Sep. 13, 2005, now Pat. No. 7,148,024.

(60) Provisional application No. 60/609,846, filed on Sep. 15, 2004.

(51) Int. Cl.
*C07K 1/13* (2006.01)
*C07K 1/10* (2006.01)
*G01N 33/532* (2006.01)
*G01N 33/544* (2006.01)
*G01N 33/53* (2006.01)

(52) U.S. Cl. ............... 530/403; 530/402; 530/405; 530/408; 530/807; 436/56; 436/544; 436/528; 435/7.1; 435/7.92; 435/7.93

(58) Field of Classification Search ................. 530/403, 530/402, 405, 408, 807; 436/56, 544, 528; 435/7.1, 7.92, 7.93
See application file for complete search history.

(56) References Cited

U.S. PATENT DOCUMENTS 5,430,057 A    7/1995    Anderson et al.

OTHER PUBLICATIONS

Murdter et al. Sensitive and rapid quantification of Busulfan in small plasme volumes by liquid chromatography electrospray mass spectrometry. Clinical Chemistry 2001, vol. 47, pp. 1437-1442, whole document.
Lai et al. Routine analysis of plasma busulfan by gas chromatography-mass freagmentography. Clinical Chemistry 1998, vol. 44, pp. 2506-2510, whole document.
Reis et al. Development of a rapid and specific assay for detection of busulfan in human plasma by high performance liquid chromatorgraphy/electrospray ionization tandem mass spectometry. Rapid Communication in Mass Spectrometry. 2004, vol. 19, pp. 1666-1674.
The International Preliminary Report on Patentability by the International Bureau of WIPO, issued on Mar. 29, 2007, in the PCT application No. PCT/US2005/032789.

*Primary Examiner*—Long V. Le
*Assistant Examiner*—Shafiqul Haq

(57) ABSTRACT

Novel conjugates of busulfan and novel busulfan immunogens derived from α-substituted derivatives of busulfan and antibodies generated by these busulfan linked immunogens are useful in immunoassays for the quantification and monitoring of busulfan in biological fluids.

17 Claims, No Drawings

BUSULFAN IMMUNOASSAY

CROSS-REFERENCE TO RELATED APPLICATION

This application is a Divisional of application Ser. No. 11/225,613 filed Sep. 13, 2005 now U.S. Pat. No. 7,148,024. This Application claims the benefit of Provisional Application Ser. No. 60/609,846 filed Sep. 15, 2004.

FIELD OF THE INVENTION

This invention relates to the field of immunological assays for determining the presence and/or quantifying the amount of busulfan in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Busulfan is a commonly used cytotoxic agent that is used for the treatment of Chronic myelogenous leukemia and high-dose pre-transplant conditioning. This chemotherapeutic agent has the formula:

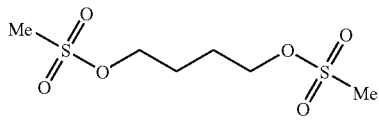

This compound has been associated with debilitating side effects such as mucositis, hepatic veno-occlusive disease and myelosuppression. By monitoring the levels of busulfan in the body and adjusting the dose these side effects can be better controlled and limited in patients.

At the same time, there is often high variable relationship between the dose of busulfan and the resulting serum drug concentration that affects therapeutic effect. The degree of intra- and inter-individual pharmacokinetic variability of busulfan can be as high as 10-fold (Slattery et. al. Blood 89(8): pp 3055-3060) and is impacted by many factors (Gurney et. al., J. Clin. Oncol. 14, pp 2590-2611, 1996), including:

Organ function
Genetic regulation
Disease state
Age
Drug-drug interaction
Time of drug ingestion,
Mode of drug administration, and
Technique-related administration.

As a result of this variability, equal doses of the same drug in different individuals can result in dramatically different clinical outcomes (Hon et. al. *Clinical Chemistry* 44, pp 388-400, 1998). The effectiveness of the same busulfan dosage varies significantly based upon individual drug clearance and the ultimate serum drug concentration in the patient. Therapeutic drug management would provide the clinician with insight on patient variation in both oral and intravenous drug administration. With therapeutic drug management, drug dosages could be individualized to the patient, and the chances of effectively treating the cancer without the unwanted side effects would be much higher (Nieto, *Current Drug Metabolism* 2: pp 53-66, 2001).

In addition, therapeutic drug management of busulfan would serve as an excellent tool to ensure compliance in administering chemotherapy with the actual prescribed dosage and achievement of the effective serum concentration levels. It has been found that variability in serum concentration is not only due to physiological factors, but can also result from variation in administration technique.

Routine therapeutic drug management of busulfan would require the availability of simple automated tests adaptable to general laboratory equipment. Current testing for Busulfan involves gas chromatography/mass spectrometry (Slattery et. al., Bone Marrow Transplant 16: pp 31-42, 1995). GC/MS is labor intensive and expensive. Tests that would best fit the criteria of simplicity and availability are immunoassays. In order to be most effective in monitoring drug levels the antibody should be most specific to the active compound and display very low cross-reactivity to no cross-reactivity to the non-active blocking metabolites particularly tetramethylene sulfone, tetrahydrothiophene and tetrahydrothiophene-3-ol-1,1-dioxide[tetrahydro-3-thiophenol1,1-dioxide].

SUMMARY OF INVENTION

In accordance with this invention, a new class of antibodies have been produced which are substantially selectively reactive to busulfan so as to bind to busulfan without any substantial cross reactivity to busulfan metabolites, particularly tetramethylene sulfone, tetrahydrothiophene and tetrahydrothiophene-3-ol-1,1-dioxide. By selectively reactive it is meant that this antibody only reacts with the busulfan molecule and does not substantially react with the blocking busulfan metabolites, which are tetramethylene sulfone, tetrahydrothiophene and tetrahydrothiophene-3-ol-1,1-dioxide. [tetrahydro-3-thiophenol1,1-dioxide].

It has been found that by using immunogens which are conjugates of an immunogenic polyamine polymer with a compound of the formula II-A:

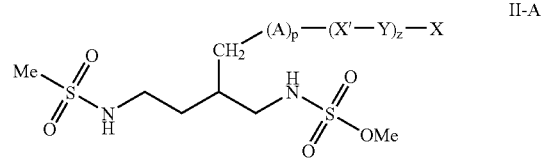

wherein A is lower alkylene;
X' is a functional linking group;
Y is an organic spacing group;
X is a terminal functional group capable of binding to a polyamine polymer;

p and z are independent integers of from 0 to 1;
compounds of the formula II-B

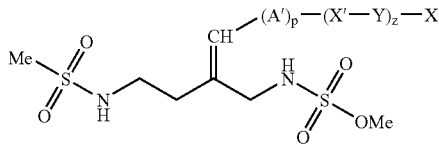

II-B wherein A' is lower alkylene or lower alkenylene;
X', Y, X, p and z are as above or mixtures thereof.

produce antibodies which are specific for busulfan and do not substantially react with or bind to the blocking metabolites of busulfan, which are tetramethylene sulfone, tetrahydrothiophene and tetrahydrothiophene-3-ol-1,1-dioxide. The provision of these antibodies which substantially selectively react with busulfan and do not cross react with tetramethylene sulfone, tetrahydrothiophene and tetrahydrothiophene-3-ol-1,1-dioxide allows one to produce an immunoassay which can specifically detect and monitor busulfan in the fluid samples of patients being treated with busulfan. Also included within this invention are reagents and kits for said immunoassay.

DETAILED DESCRIPTION

In accordance with this invention, a new class of antibodies is provided which substantially selectively reacts with busulfan and do not substantially react or cross react with the busulfan metabolites mentioned hereinabove. It has been discovered that through the use of these a-substituted busulfan derivatives of formulae II-A and II-B as immunogens, this new class of antibodies of this invention are provided. It is through the use of these antibodies that an immunoassay, including reagents and kits for such immunoassay for detecting and/or quantifying busulfan in blood, plasma or other body fluid samples has been developed. By use of this immunoassay, the presence and amount of busulfan in body fluid samples, preferable a blood or plasma sample, can be detected and/or quantified. In this manner, a patient being treated with busulfan can be monitored during therapy and his treatment adjusted in accordance with said monitoring. By means of this invention one achieves the therapeutic drug management of busulfan in cancer patients being treated with busulfan as a chemotherapeutic agent.

The reagents utilized in the assay of this invention are conjugates of a polymeric carrier with the compounds of formulae II-A and II-B. These conjugates are competitive binding partners with the busulfan present in the sample for the binding with the antibodies of this invention. Therefore, the amount of conjugate reagent which binds to the antibody will be inversely proportional to the amount of busulfan in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of busulfan in a sample is determined by correlating the measured amount of the bound or unbound conjugate produced by the busulfan in the sample with values of the bound or unbound conjugate determined from standard or calibration curve samples containing known amounts of busulfan, which known amounts are in the range expected for the sample to be tested. These studies for producing calibration curves are determined using the same immunoassay procedure as used for the sample.

The conjugates, as well as the immunogens, are prepared from compounds of the formulae II-A and II-B. The conjugates of the carrier or immunogens are linked to the polyamine polymer ligand portions of the compound of formula II-A and II-B where X is X'. These ligand portions may be linked to one or more active sites on the carrier or polyamine polymer of the immunogen.

Definitions

Throughout this description the following definitions are to be understood:

The term "Me" as used throughout this application designates a methyl radical. The term "lower alkylene" designates a divalent saturated straight or branch chain hydrocarbon substituent containing from one to six carbon atoms. The term "lower alkenylene" designates a divalent straight or branch chain hydrocarbon group containing from two to six carbon atoms and an unsaturated double bond in the hydrocarbon chain.

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II and a large molecule, such as a carrier or a polyamine polymer, particularly protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is busulfan.

As used herein, a "spacing group" or "spacer" refers to a portion of a chemical structure which connects two or more substructures such as haptens, carriers, immunogens, labels, or tracers through a $CH_2$ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer .

An "immunogenic carrier," as the terms are used herein, is an immunogenic substance, commonly a protein, that can join with a hapten, in this case busulfan or the busulfan derivatives hereinbefore described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino- polysaccharides, particles, and nucleic acids that are recognized as foreign and thereby elicit an immunologic response from the host. The polyamino- polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as *erythrocytes, leukocytes, lymphocytes, hybridomas Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the NH2 terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins. A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula II.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for busulfan. The kit may further comprise ligands of the analyte and calibration and control materials. The reagents may remain in liquid form or may be lyophilized. The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of busulfan is constructed to compete with the busulfan in the sample for binding sites on the antibodies. In the immunoassay of this invention, the reagents are the a-substituted busulfan derivatives of the compounds of formulae II-A and II-B where the terminal functional group X is converted to X", which like X' is a functional linking group, which links the ligand to the polyamine polymer. In the compounds of formulae II-A and II-B, the linker spacer constitutes the —(X'—Y)$_z$— portion of these molecules. These linkers are designated as X' and the spacer is designated as —Y— in preparing conjugates and immunogens. Any of the conventional spacer-linking groups utilized to prepare conjugates and immunogens for immunoassays can be utilized in the compounds of formulae II-A and II-B. Such conventional linkers and spacers are disclosed in U.S. Pat. Nos. 5,501,987 and 5,101,015.

In accordance with the embodiment of this invention z in the compounds of formula II-A and II-B can be 0. Therefore, the compounds of formulae II-A and II-B need not contain any spacer group and the X can be directly connected to the remainder of the molecule within the compounds of formulae II-A and II-B.

Among the preferred spacer groups are included the spacer groups hereinbefore mentioned. Particularly preferred spacing groups are groups such as alkylene or alkenylene which contain from 1 to 10 carbon atoms, or

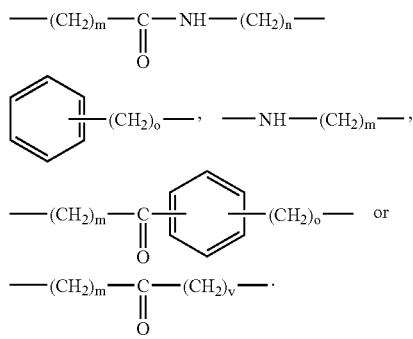

wherein n and o are integers from 0 to 6 and m and v are integers from 1 to 6 with alkylene being the especially preferred spacing group.

In the forming the conjugates from the compounds of formulae II-A and II-B, X' and X" are preferably —$CH_2$— or a functional group linking the spacer, preferably to an amine group on the polymeric carrier. The group X" is the result of the terminal functional group X in the compounds of formulae II-A and II-B which is capable of binding to the amino group in the polyamine polymer used for bonding the carrier or the immunogen. Any terminal functional group capable of reacting with an amine can be utilized as the functional group X in the compounds of formula II. These terminal functional groups preferably included within X are:

$$-\overset{\text{O}}{\underset{\|}{\text{C}}}-OR_3, \quad -N=C=R_4, \quad \text{or} \quad -\overset{\text{O}}{\underset{\|}{\text{CH}}}$$

wherein $R_3$ is hydrogen or taken together with its attached oxygen atom forms a reactive ester and $R_4$ is oxygen or sulfur. The radical —N=C=$R_4$, can be an isocyanate or as isothiocyanate. The active esters formed by $OR_3$ include imidoester, such as N-hydroxysuccinamide, 1-hydroxy benzotriazole and p-nitrophenyl ester. However any active ester which can react with an amine group can be used.

The carboxylic group and the active esters, i.e.,

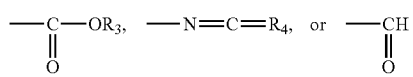

are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing busulfan haptens and the amino groups on the polyamine polymer on the carrier or immunogen can be established using a variety of methods known to one skilled in the art. It is frequently preferable to form amide bonds. Amide bonds are formed by first activating the carboxylic acid moiety of the busulfan hapten in the compound of formula II by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the busulfan hapten of formula II is then reacted with a buffered solution containing the protein carrier.

In cases where the busulfan derivative of formulae II-A and/or II-B contains a primary or secondary amino group as well as the carboxyl group, it is necessary to use an amine protecting group during the activation and coupling reactions to prevent the conjugates from reacting with themselves. Typically, the amines on the conjugate are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. Nos. 3,996,344 and 4,016,146, which are herein incorporated by reference.

On the other hand where X is an isocyanate or thioisocyanate radical in the compound of formula II-A or II-B, these radicals when reacted with the free amine of a polyamine polymer produce the conjugate or immunogen where X' or X" is, in the ligand portions of formulae II-A or II-B,

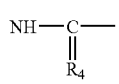

are functionally connecting with the amino group on the polyamine carrier or the immunogenic polypeptide. X' or X" form the spacer groups.

Where X, in the compounds of formula II-A or II-B, is an aldehyde group these compounds may be connected to the amine group of the polyamine polypeptide or carrier or the spacer group through an amine linkage by reductive amination. Any conventional method of condensing an aldehyde with an amine such as through reductive amination can be used to form this linkage. In this case, X' or X" in the ligand portions of formulae II-A and II-B become —$CH_2$—.

The compounds of formulae II-A and II-B are prepared from a compound of the formula:

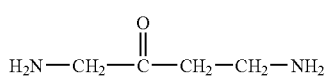

by first protecting the two primary amine groups in the compound of formula V with a conventional amino protecting group. Any conventional amino protecting group can be used in protecting the compound of formula V. The preferred amino protecting group is Boc[tertiary butoxycarbonyl]. Any conventional method of reacting an amine to form these protecting amine groups can be used in this process.

In this next step the protected amine of the compound of formula V is reacted via a Horner or Wittig type reaction with a compound of the formula:

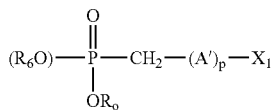
VI wherein A' and p are as above; and $R_6$ is lower alkyl and $X_1$ is a terminal functional group capable of binding to a polyamine polymer.

to form a compound of the formula:

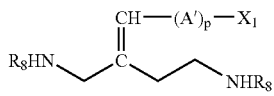
VII wherein $X_1$, A' and p are as above; and $R_8$ is an amino protecting group.

If it is desired to produce the compounds of formulae II-A or II-B with a linker spacer group X'—Y, the compound of formula VII reacted with a compound of the formula:

$R_{10}YX$      VIII wherein $R_{10}$ is halo or $NH_2$;

X is a terminal functional group capable of reacting with a polyamine polymer; and Y is as above.

In this case where $X_1$ in the compound of formula VIII is a reactive acid derivative, it is protected by forming a conventional ester protecting group. The reaction of the compound of formulae VII and VIII produces a compound of the formula:

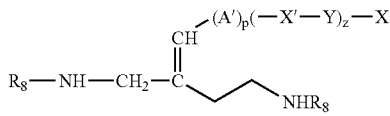
IX wherein $R_8$, A', p, X', Y, X and z are as above.

The reaction of compound of the formula VII and VIII to produce the compound of formula IX depending upon the functional group X, in the compound of formula VII, is carried out by any means such as condensing an isocyanate, isothiocyanate, active ester, acid or aldehyde group as described hereinbefore with a halide or amine.

If it is decided to produce the compound of formula II-A, the double bonds in the compound of formula IX are hydrogenated to reduce them to a saturated bond by conventional means. This will produce a compound of the formula:

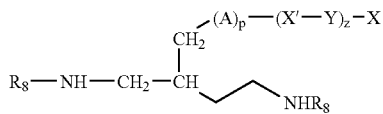
X wherein A, z, p, X', Y and X are as above.

Any conventional method of hydrogenation can be carried out to convert the compound of formula IX to the compound of formula X. Generally this reaction is carried out with hydrogen utilizing a paladium on carbon catalyst. This reduction via hydrogenation not only reduces the double bond between the attachment to the chain of the protected diamine but reduces all double bonds in the substituent Y. If it is desired to produce a spacer Y substituent with a double bond, the compound of formula VII can be first reduced by hydrogenation such as described above to produce a compound of the formula:

VII-A wherein $R_8$, A, p and $X_1$ are as above and reacted with the compound of formula VIII to obtain the compound of formula X wherein Y is a substituent containing at least one double bond.

In the next step of this invention, the amino protecting groups are removed from the compound of formula IX or formula X by any conventional means of removing such groups to form the compound of the formula:

XI wherein A, p, z, X' and X are as above; or

XII wherein A', p, z and X are as above.

This can be done by conventional acidic hydrolysis such as with trifluoro acetic acid which is especially suitable for such amino protecting groups and will convert the amino groups into their acid addition amino salts. These amino salts of the compounds of Formula XI and XII can be respectively converted into the compounds of Formula II-A and formula II-B by mesylation through reaction with methylsulphonyl chloride (mesylchloride). In this manner mesyl groups are introduced at each the two terminal amino groups in the compounds of Formula XI and XII.

In carrying out this reaction, it is best in the compounds of formula IX, X, XI and XII to protect the free reactive acid derivatives via an ester protecting group. In forming the compound of formula II-A and II-B after mesylation, the acid protecting groups can be removed by acid hydrolysis.

The compound of formulae II-A and II-B can be converted into the immunogens and/or the conjugate reagents of this invention by reacting these compounds with a polyamine or polypeptides. The same polypeptide can be utilized as the carrier and as the immunogenic polymer in the immunogen of this invention provided that the polyamine or polypeptide is immunologically active. However, to form the conjugates, these polymers need not produce an immunological response as needed for the immunogens. In accordance with this invention, the various functional group represented by X in the compounds of formulae II-A and II-B can be conjugated to the polymeric material by conventional means of attaching a functional group to an amine group contained within the polymer. In accordance with the preferred embodiment, in the compound of formulae II-A and II-B, X is a carboxylic acid group.

Antibodies

The present invention also relates to novel antibodies including monoclonal antibodies to busulfan produced by utilizing the aforementioned immunogens. In accordance with this invention it has been found that these antibodies produced in accordance with this invention are selectively reactive with busulfan and do not react with metabolites which would interfere with immunoassays for busulfan. The ability of the antibodies of this invention not to react with these tetramethylene sulfone, tetrahydrothiophene and tetrahydrothiophene-3-ol-1,1-dioxide metabolites makes these antibodies particularly valuable in providing an immunoassay for busulfan.

The present invention relates to novel antibodies and monoclonal antibodies to busulfan. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and two or more subsequent booster shots of between 50 and 100 ug immunogen/mouse over a six month period. Through periodic bleeding, the blood samples of the immunized mice were observed to develop an immune response against busulfan binding utilizing conventional immunoassays. These methods provide a convenient way to screen for hosts which are producing antisera having the desired activity. The antibodies were also screened against metabolites of busulfan and showed no substantial binding to these compounds.

Monoclonal antibodies are produced conveniently by immunizing Balb/c mice according to the above schedule followed by injecting the mice with 100 ug immunogen i.p. or i.v. on three successive days starting four days prior to the cell fusion. Other protocols well known in the antibody art may of course be utilized as well. The complete immunization protocol detailed herein provided an optimum protocol for serum antibody response for the antibody to busulfan.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce busulfan monoclonal antibodies are formed by the fusion of mouse myeloma cells and spleen cells from mice immunized against busulfan-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are selective for busulfan without having any substantial cross-reactivity with the blocking metabolites of busulfan which are tetramethylene sulfone, tetrahydrothiophene and tetrahydrothiophene-3-ol-1,1-dioxide By not having any substantial cross-reactivity, it is meant that the antibodies of this invention have a cross reactivity relative to busulfan with these blocking metabolites of less than 10%, preferably less than 5%.

Immunoassays

In accordance with this invention, the conjugates and the antibodies generated from the immunogens of these compounds of formula II or mixtures thereof can be utilized as reagents for the determination of busulfan in patient samples. This determination is performed by means of an immunoassay. Any immunoassay in which the reagent conjugates formed from the compound of formula II compete with the busulfan in the sample for binding sites on the antibodies generated in accordance with this invention can be utilized to determine the presence of busulfan in a patient sample. The manner for conducting such an assay for busulfan in a sample suspected of containing busulfan, comprises combining an (a) aqueous medium sample, (b) an antibody to busulfan generated in accordance with this invention and (c) the conjugates formed from the compound of formula II or mixtures thereof. The amount of busulfan in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of busulfan. In determining the amount of busulfan in an unknown sample, the sample, the conjugates formed from the compound of formula II and the antibody may be added in any order.

Various means can be utilized to measure the amount of conjugate formed from the compound of formula II bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. Nos. 4,269,511 and 4,420,568. In this case the sample is a liquid sample and the antibody is soluble in the aqueous media containing the sample and the conjugate.

On the other hand, the antibody can be coated or absorbed on nanoparticles so that when these particles react with the busulfan conjugates formed from the compounds of formula II, these nanoparticles form an aggregate. However, when the antibody coated or absorbed nanoparticles react with the busulfan in the sample, the busulfan from the sample bound to these nanoparticles does not cause aggregation of the antibody nanoparticles. The amount of aggregation or agglutination can be measured in the assay mixture by absorbance.

On the other hand, these assays can be carried out by having either the antibody or the busulfan conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compound of formula II which is bound or unbound with the antibody. Other suitable labels include chromophores, fluorophores, etc.

As a matter of convenience, assay components of the present invention can be provided in a kit, a packaged combination with predetermined amounts of new reagents employed in assaying for busulfan. These reagents include the antibody of this invention, as well as, the conjugates formed from the compound of formula II.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, lyophilized, including excipients which on dissolution will provide for a reagent solution having the appropriate concentrations for performing the assay.

EXAMPLES

In the examples, Me represents methyl. In the examples, the following abbreviations are used for designating the following:

| | |
|---|---|
| THF | Tetrahydrofuran |
| TEA | Triethyl amine |
| TFA | Trifluoroacetic acid |
| EtOAc | Ethyl Acetate |
| NHS | N-hydroxy succinimide |
| MeOH | Methanol |
| EDC | 1-(3-dimethylaminopropyl)-3-ethylcarbodiimide hydrochloride |
| TLC | Thin Layer Chromatrography |
| ANS | 8-Anilino-1-naphthalenesulfonic acid |
| i.p. | Intraperitoneal |
| HRP | horse radish-peroxidase |
| TMB | 3,3',5,5'-Tetramethylbenzidine |
| TRIS | Tris(hydroxymethyl)aminomethane hydrochloride |
| BSA | Bovine serum albumin |
| BTG | Bovine thyroglobulin |
| KLH | Keyhold Limpet Hemocyanin |
| PBS | Phosphate buffered saline |
| di | deionized water |

In the examples, Scheme 1 and Scheme 2 below set forth the specific compounds prepared and referred to by numbers in the Examples. The schemes are as follows:

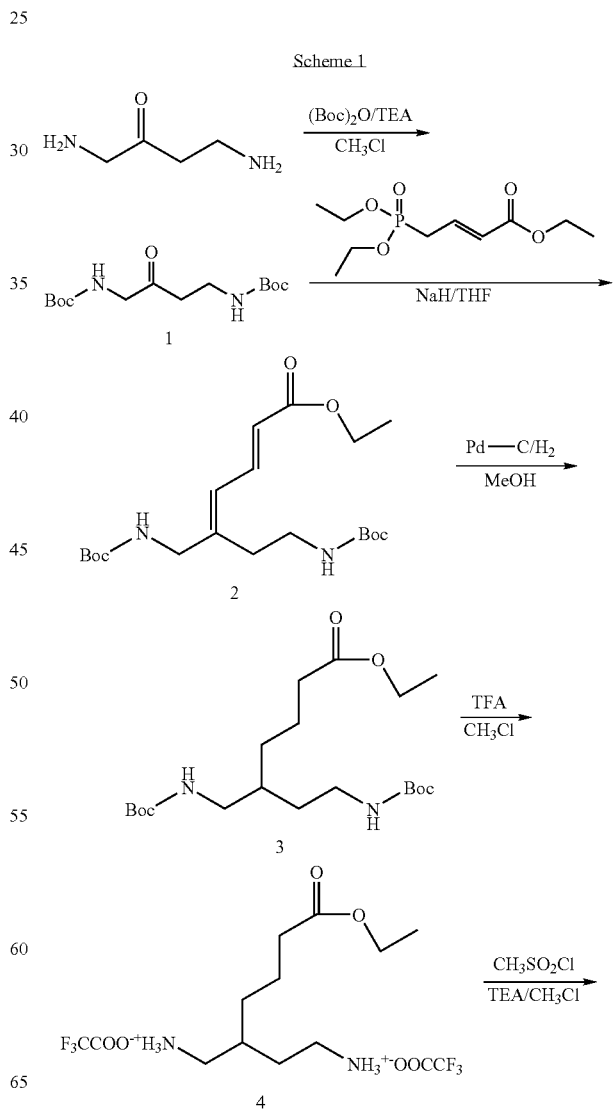

Scheme 1

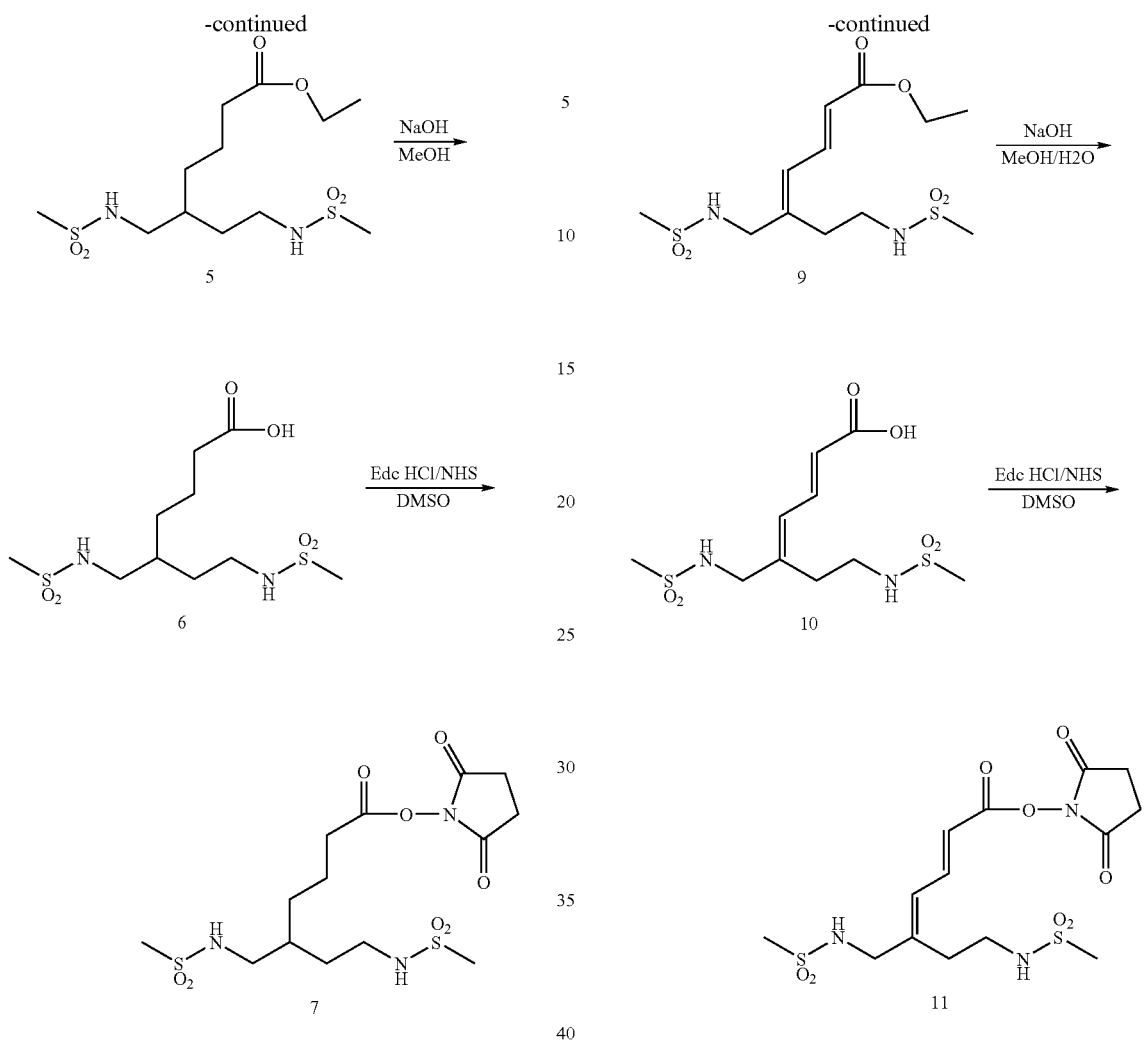

Example 1

Preparation of Busulfan Derivative [7] (Scheme 1)

To a suspension of 1,4-diamino-2-butanone dihydrochloride (0.193 g, 1.1 mmol) and TEA (0.76 mL, 5 eq) in 8 mL of chloroform was added dropwise di-tert-butyldicarbonate (0.48 g, 2 eq.) in 2 mL of chloroform. The resulting mixture was refluxed for 3 hours, cooled to room temperature, diluted with 50 mL of chloroform, and washed with 1 N HCl (2×15 mL), $H_2O$ (20 mL), Saturated $NaHCO_3$ (25 mL), and brine (30 mL), then dried over sodium sulfate for ½ hour. Concentration of the organic layer gave the product [1] (yellow solid, 95% yield). The product's structure was confirmed by NMR.

To a solution of [1] (0.9 g, 3 mmol) and triethyl 4-phosphonocrotonate (1.6 mL, 2.2 eq) in 15 mL of dry THF was added sodium hydride (0.26 g, 2.2 eq.) by portions. The resulting mixture was stirred at room temperature for 2 hours. TLC showed that the reaction was not totally complete. Removal of the solvent yielded a residue, which was taken up with EtOAc (80 mL), washed with $H_2O$ (2×40 mL), brine (40 mL), and dried over sodium sulfate for ½ hour. Concentration of the organic layer gave the crude product [2] (brown oil),

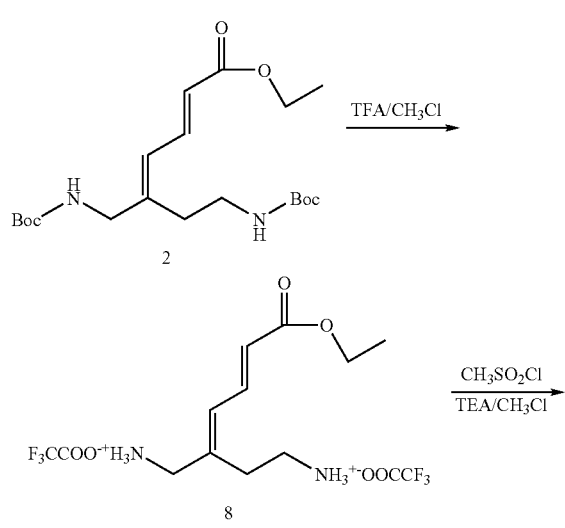

Scheme 2 which was purified by flash column chromatography with EtOAc/Hexane solvent system (20 % yield). The structure of the product was confirmed by NMR.

A solution of compound [2] (500 mg, 1.25 mmol) in 15 mL of MeOH was hydrogenated on 20% (w/w) Pd-C under atmospheric pressure for 12 hours. The mixture was diluted with 20 mL of MeOH, filtered through filter paper, and concentrated to produce 300 mg of the product [3] in 60% yield, with structural confirmation by NMR.

To a suspension of compound [3] (300 mg, 0.75 mmol) in 1 mL of chloroform was added 4 mL of trifluoroacetic acid. The resulting mixture was stirred at room temperature for 1 hour. Removal of the solvent and extra TFA yielded compound [4] as a brown oil, which was used in the next step reaction without further purification (100% yield).

To a suspension of compound [4] (0.32 g, 0.75 mmol), TEA (2.1 mL, 20 eq.) in 10 mL of chloroform with stirring in an ice-water bath was added dropwise methane sulfonyl chloride (0.6 mL, 10 eq) in 5 mL of chloroform. The resulting mixture was allowed to warm up to room temperature and stirred at room temperature overnight. Removal of the solvent yielded the crude product (brown oil), which was purified by flash column chromatography with EtOAc/ Hexane solvent system to yield [5] (140 mg, 52% yield) with structural confirmation by NMR.

A mixture of the ethyl ester busulfan derivative [5] (140 mg, 0.34 mmol) and sodium hydroxide (110 mg, 7 eq) in methanol/water (4:1, 10 ml) was refluxed for 2 hours, diluted with 10 mL of $H_2O$ and acidified with 1 N hydrochloric acid to pH 1. Removal of the solvent yielded the crude product, which was taken up with 6 ml of MeOH. Filtering off of the NaCl salt and concentration of the filtrate produced the product [6] in 100% yield, with structural confirmation by NMR.

To a solution of busulfan acid derivative [6] (120 mg, 0.36 mmol) in 3 ml of DMSO was added EDC·HCl (209 mg, 3 eq.), and NHS (125 mg, 3 eq.). The reaction mixture was stirred at room temperature overnight under nitrogen to produce compound [7]. The crude reaction mixture was used for protein conjugations of examples 3, 4 and 5.

Example 2

Preparation of Busulfan Derivative [11] Scheme 2

To a suspension of compound [2] from example 1 (0.43 g, 1.08 mmol) in 1 mL of chloroform was added 4 mL of trifluoroacetic acid. The resulting mixture was stirred at room temperature for ½ hour. Removal of the solvent and extra TFA yielded compound [8] as a brown oil; structure was confirmed by NMR. This material was used in the next reaction without further purification (100% yield).

To a suspension of compound [8] (0.43 g, 1 mmol), with TEA (2.8 mL, 20 eq.) in 10 mL of chloroform in an ice-water bath was added drop wise methane sulfonyl chloride (0.8 mL, 10 eq) in 5 mL of chloroform. The resulting mixture was allowed to warm up to room temperature and stirred at room temperature overnight. Removal of the solvent yielded the crude product [9] (brown oil), which was purified by flash column chromatography with EtOAc/Hexane solvent system (30% yield). The structure was confirmed by NMR.

A mixture of the ethyl ester [9] (160 mg, 0.45 mmol) and sodium hydroxide (110 mg, 7 eq) in methanol/water (4:1, 10 ml) was refluxed for 2 hours, diluted with 10 mL of $H_2O$ and acidified with 1 N hydrochloric acid to pH 1. Removal of the solvent yielded the crude product, which was taken up with 6 ml of MeOH. Filtering off the NaCl salt and concentration of the filtrate produced the product [10] (100% yield). The structure was confirmed by NMR.

To the solution of busulfan acid derivative [10] (50 mg, 0.15 mmol) in 2 ml of DMSO was added EDC·HCl (88 mg, 3 eq.), and NHS (52 mg, 3 eq.). The reaction mixture was stirred at room temperature overnight, under nitrogen to produce the activated NHS ester [11]. The crude reaction mixture was used for the protein conjugations of example 6.

Example 3

Preparation of Busulfan BTG Immunogen

To 17 mL of BTG (21.2 mg/mL) in 50 mM phosphate buffer (50 mM, pH 7.5)0.625 mL of the activated N-Hydroxysuccinimide ester busulfan derivative [7] prepared in example 1 (40 mg/mL in DMSO) was added drop wise while stirring the solution in an ice bath. The resulting mixture was allowed to stir overnight at room temperature to conjugate the BTG to the busulfan derivative [7]. This immunogenic conjugate was then purified by dialysis and characterized according to procedures described previously (Wu et. al., Bioconj. Chem., 8: pp 385-390,1997, Li et. al., Bioconj. Chem., 8: pp 896-905, 1997, Salamone et.al., J. Forensic Sci. pp 821-826, 1998).

Example 4

Preparation of Busulfan KLH Immunogen

To 24 mL of KLH (20.8 mg/mL) in 50 mM phosphate buffer (50 mM, pH 7.5) 0.9 mL of the activated N-Hydroxysuccinimide ester busulfan derivative [7] prepared in example 1 (40 mg/mL in DMSO) was added drop wise while stirring the solution in an ice bath. The resulting mixture was allowed to stir overnight at room temperature to conjugate the KLH to the busulfan derivative [7]. This immunogenic conjugate was then purified by dialysis and characterized according to procedures described previously (Wu et. al., Bioconj. Chem., 8: pp 385-390,1997, Li et.al., Bioconj. Chem., 8: pp 896-905,1997, Salamone et.al., J. Forensic Sci. pp 821-826, 1998).

Example 5

Preparation of Busulfan-BSA Conjugate with Derivative 7

To a 20 mL solution of BSA (50 mg/mL) in phosphate buffer (50 mM, pH 7.5) 0.9 mL of the activated N-Hydroxysuccinimide ester busulfan derivative [7] prepared in example 1 (40 mg/mL in DMSO) was added drop wise while stirring the solution in an ice bath. The mixture was allowed to stir overnight at room temperature to produce the conjugate of the activated ester [7] and BSA. This conjugate was then purified by dialysis and characterized according to procedures described previously (Wu et. al., Bioconj. Chem., 8: pp 385-390, 1997, Li et.al., Bioconj. Chem., 8: pp 896-905, 1997, Salamone et.al., J. Forensic Sci. pp 821-826, 1998).

Example 6

Preparation of Busulfan-BSA Conjugate with Derivative 11

To a 20 mL solution of BSA (50 mg/mL) in phosphate buffer (50 mM, pH 7.5) 0.2 mL of the activated N-Hydroxysuccinimide ester busulfan derivative [11] prepared in example 2 (25 mg/mL in DMSO) was added drop wise while stirring the solution in an ice bath. The mixture was allowed to stir overnight at room temperature to produce the conjugate of the activated ester [11] and BSA. This conjugate was then purified by dialysis and characterized according to procedures described previously (Wu et. al., Bioconj. Chem., 8: pp 385-390,1997, Li et.al., Bioconj. Chem., 8: pp 896-905,1997, Salamone et.al., J. Forensic Sci. pp 821-826, 1998).

Example 7

Preparation of Busulfan Antibodies

Ten Female BALB/c mice were immunized i.p. with 100 μg/mouse of Busulfan-BTG immunogen prepared in example 3 or with Busulfan-KLH immunogen prepared in example 4, emulsified in Complete Freund's Adjuvant. Mice were boosted once four weeks after the initial injection with 100 μg/mouse of the same immunogens emulsified in Incomplete Freund's Adjuvant. Ten or 28 days after the boost test bleeds from each mouse were obtained by orbital bleed. The antiserum from these test bleeds contained Busulfan antibodies evaluated in Examples 9, 10a and 10b.

Example 8a

Microtiter Plate Sensitization Procedure with Busulfan Derivative 7—BSA Conjugate The ELISA method for measuring busulfan concentrations was performed in polystyrene microtiter plates (Nunc MaxiSorp C8 or F8 Immunomodules) optimized for protein binding and containing 96 wells per plate. Each well was coated with busulfan-BSA conjugate (prepared as in example 5) by adding 300 μL of busulfan-BSA conjugate at 10 μg/mL in 0.05M sodium bicarbonate, pH=9.6, and incubating for three hours at room temperature. The wells were washed with 0.05M sodium bicarbonate, pH 9.6 and then were blocked with 400 μL of 5% sucrose, 0.2% sodium caseinate solution for 30 minutes at room temperature. After removal of the post-coat solution the plates were dried at 37° C. overnight.

Example 8b

Microtiter Plate Sensitization Procedure with Busulfan Derivative 11—BSA Conjugate The ELISA method for measuring busulfan concentrations was performed in polystyrene microtiter plates (Nunc MaxiSorp C8 or F8 Immunomodules) optimized for protein binding and containing 96 wells per plate. Each well was coated with busulfan-BSA conjugate (prepared as in example 6) by adding 300 μL of busulfan-BSA conjugate at 2.5 μg/mL in 7.5 ·g/mL BSA, 0.05M sodium bicarbonate, pH=9.6, and incubating for three hours at room temperature. The wells were washed with 0.05M sodium bicarbonate, pH 9.6 and then were blocked with 400 μL of 5% sucrose, 0.2% sodium caseinate solution for 30 minutes at room temperature. After removal of the post-coat solution the plates were dried at 37° C. overnight.

Example 9

Antibody Screening Procedure—Titer

The ELISA method for screening busulfan antibodies (produced in example 7) was performed with the microtiter plates that were sensitized with busulfan-BSA as described in examples 8a and 8b. The antibody screening assay was performed by diluting the antisera containing busulfan antibodies (of example 7) to 1:100, 1:1,000, 1:10,000 and 1:100,000 in phosphate buffered saline containing 0.1% BSA and 0.01% thimerosal. To each well of busulfan-BSA sensitized wells (prepared in examples 8a and 8b) 100 μL of diluted antibody was added and incubated for 10 minutes at room temperature with shaking. During this incubation antibody binds to the busulfan-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of busulfan antibody bound to the busulfan-BSA conjugate in the wells 100 μL of a goat anti-mouse antibody—HRP enzyme conjugate (Jackson Immunoresearch) diluted to a predetermined specific activity (approximately 1/2000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the secondary-HRP conjugate binds to busulfan antibodies in the wells, the plates were again washed three times to remove unbound secondary conjugate. To develop a measurable color in the wells, washing was followed by the addition of 100 μL of TMB (TMB Liquid Substrate, Sigma), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing Log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in examples 10a and 10b.

Example 10a

Indirect Competitive Microtiter Plate Immunoassay Procedure with Busulfan Derivative 7—BSA Sensitized Plates Determining $IC_{50}$ and Cross-Reactivity The ELISA method for measuring busulfan concentrations was performed with the microtiter plates that were sensitized with busulfan derivative 7-BSA described in example 8a.

Busulfan, tetramethylene sulfone, tetrahydrothiophene andtetrahydrothiophene-3-ol-1,1-dioxide were diluted 10 fold in PBS or PBS containing 0.1% BSA and 0.01% thimerosal over a concentration range of 0.01 to 100,000 ng/mL. The assay was performed by incubating 50 μL of the analytes to be measured with 50 μL of antibody (produced in example 7) diluted to a titer determined in example 9. During the 10 minute incubation (R.T., with shaking) there is a competition of antibody binding for the busulfan conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of busulfan antibody bound to the busulfan-BSA conjugate in the wells, 100 μL of a secondary antibody which was a goat anti mouse anti-globulin antibody—HRP enzyme conjugate (Jackson Immunoresearch) diluted to a predetermined specific activity (approximately ½000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the secondary-HRP conjugate binds to busulfan antibodies in the wells, the plates were again washed three times to remove unbound secondary conjugate. To develop a measurable color in the wells, washing was followed by the addition of 100 μL of TMB (TMB Liquid Substrate, Sigma), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of busulfan in the sample. The absorbance of the color in the wells containing analyte is compared to that with no analyte and a standard curve is generated. The $IC_{50}$ value for a given analyte was defined as the concentration of analyte that is required to inhibit 50% of the absorbance for the wells containing no analyte. The cross-reactivity of a given analyte was calculated as the ratio of the $IC_{50}$ for busulfan to the $IC_{50}$ for tetramethylene sulfone, tetrahydrothiophene and tetrahydrothiophene-3-ol-1,1-dioxide as a percent. When measured with an antibody as produced in example 7 with immunogen of examples 3 & 4 the percent cross-reactivates relative busulfan for tetramethylene sulfone, tetrahydrothiophene and tetrahydrothiophene-3-ol-1,1-dioxide were less than 5%. Results are in table 1 below.

Example 10b

Indirect Competitive Microtiter Plate Immunoassay Procedure with Busulfan Derivative 11—BSA Sensitized Plates Determining $IC_{50}$ and Cross-Reactivity The ELISA method for measuring busulfan concentrations was performed with the microtiter plates that were sensitized with busulfan derivative 11-BSA described in example 8b. Busulfan, tetramethylene sulfone, tetrahydrothiophene and tetrahydrothiophene-3-ol-1,1-dioxide were diluted 10 fold in PBS or PBS containing 0.1% BSA and 0.01% thimerosal over a concentration range of 0.01 to 100,000 ng/mL. The assay was performed by incubating 50 μL of the analytes to be measured with 50 μL of antibody (produced in example 7) diluted to a titer determined in example 9. During the 10 minute incubation (R.T., with shaking) there is a competition of antibody binding for the busulfan conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of busulfan antibody bound to the busulfan-BSA conjugate in the wells, 100 μL of a secondary antibody which was a goat anti mouse anti-globulin antibody—HRP enzyme conjugate (Jackson Immunoresearch) diluted to a predetermined specific activity (approximately ½000) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the secondary —HRP conjugate binds to busulfan antibodies in the wells, the plates were again washed three times to remove unbound secondary conjugate. To develop a measurable color in the wells, washing was followed by the addition of 100 μL of TMB (TMB Liquid Substrate, Sigma), a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and inversely proportional to the amount of busulfan in the sample. The absorbance of the color in the wells containing analyte is compared to that with no analyte and a standard curve is generated. The $IC_{50}$ value for a given analyte was defined as the concentration of analyte that is required to inhibit 50% of the absorbance for the wells containing no analyte. The cross-reactivity of a given analyte was calculated as the ratio of the $IC_{50}$ for busulfan to the $IC_{50}$ for tetra-sulfone, tetrathiophene and tetrahydrothiophene-3-ol-1,1-dioxide as a percent. When measured with an antibody as produced in example 7 with immunogen of examples 3 & 4 the percent cross-reactivates relative busulfan for tetramethylene sulfone, tetrathiophene and tetrahydrothiophene-3-ol-1,1-dioxide were less than 5%. Results are in table 1 below.

TABLE 1

Cross-Reactivity of Competitive Immunoassay using antibodies to Busulfan-KLH (example 7) with plate coatings Busulfan-BSA conjugates (example 5, derivative 7 and example 6, derivative 11).

| | Microtiter Plate Sensitization | |
|---|---|---|
| Analyte | Busulfan Derivative 7 | Busulfan Derivative 11 |
| Busulfan | 100% | 100% |
| Tetramethylene sulfone | <0.4% | <0.24% |
| Tetrahydrothiophene | <0.4% | <0.24% |
| Tetrahydrothiophene-3-ol-1,1-dioxide | <0.4% | <0.24% |

As seen from the above table the antibodies of this invention are not reactive with the blocking metabolites of busulfan.

What is claimed:

1. A compound of the formula:

![Structure I showing Me-S(=O)2-NH-(CH2)-CH(CH2-(A)p-(X'-Y)z-X)-(CH2)-NH-S(=O)2-OMe]

wherein A is lower alkylene;
X' is a functional linking group;
Y is an organic spacing group;
X is a terminal functional group capable of reacting with a polyamine polymer;
p and z are independent integers of from 0 to 1.

2. The compound of claim 1, wherein X is $$-\underset{\parallel}{\underset{O}{C}}-OR_3, \quad -N=C=R_4, \quad \text{or} \quad -\underset{\parallel}{\underset{O}{C}}H$$

wherein $R_3$ is hydrogen or taken together with its attached oxygen atom forms a reactive ester and $R_4$ is oxygen or sulfur.

3. The compound of claim 2, wherein X is $$-\underset{\parallel}{\underset{O}{C}}-OR_3$$

and $R_3$ is hydrogen.

4. The compound of claim 3, wherein X is $$-\underset{\parallel}{\underset{O}{C}}-OR_3$$

and $R_3$ forms a reactive ester.

5. The compound of claim 4, wherein the ester formed is a lower alkyl ester, imidoester or amidoester.

6. The compound of claim 5, wherein z is 0 and p is 1.

7. The compound of claim 6, wherein A is $-(CH_2)_v-$ and v is 1 or 2.

8. The compound of claim 7, wherein v is 2.

9. A conjugate of a carrier with a compound of the formula:

![Structure II-A]

wherein A is lower alkylene;
X' is a functional linking group;
Y is an organic spacing group;
X is a terminal functional group capable of reacting with a polyamine polymer;
p and z are independent integers of from 0 to 1 wherein said polyamine polymer reacts with X to form said conjugate;

or a compound of the formula

![Structure II-B]

wherein A' is lower alkylene or lower alkenylene;
X', Y, X and z are as above.

10. The conjugate of a polyamine polymer with claim 9, wherein said compound is

![Structure II-A]

wherein A, X', Y, X, p and z are as above.

11. The conjugate of claim 10, wherein z is 0.

12. The conjugate of claim 11, wherein X is $$-\underset{\parallel}{\underset{O}{C}}-OR_3, \quad -N=C=R_4, \quad \text{or} \quad -\underset{\parallel}{\underset{O}{C}}H$$

wherein $R_3$ is hydrogen or taken together with its attached oxygen atom forms a reactive ester and $R_4$ is oxygen or sulfur.

13. The conjugate of claim 12, wherein the carrier contains one or more amino groups linked by

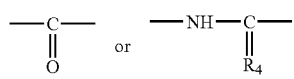

wherein $R_4$ is oxygen or sulfur.

14. The conjugate of claim 13, wherein A is —$(CH_2)_v$— and v is an integer from 1 to 3.

15. The conjugate of claim 14, wherein v is 2.

16. An immunogen containing an immunogenic polyamine polymer linked to a compound of the formula:

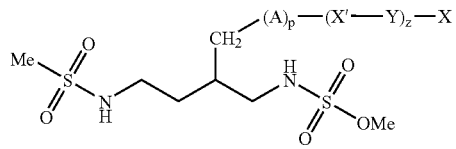

wherein A is lower alkylene;
X' is a functional linking group;
Y is an organic spacing group;
X is a terminal functional group capable of reacting with a polyamine polymer;
p and z are independent integers of from 0 to 1 wherein said immunogenic polyamine polymer reacts with X to form said immunogen;
or a compound of the formula

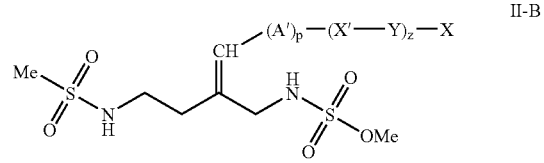

wherein A' is lower alkylene or lower alkenylene;
X', Y, X and z are as above.

17. The immunogen of claim 16, wherein the immunogenic polymer contains one or more amino groups linked by

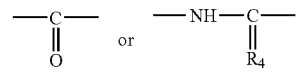

wherein $R_4$ is oxygen or sulfur.

* * * * *